United States Patent [19]

Koller et al.

[11] Patent Number: 4,612,396
[45] Date of Patent: Sep. 16, 1986

[54] PROCESS FOR THE PREPARATION OF PURE 2-ETHYLAMINO-4-NITRO-1-ALKOXYBENZENES

[75] Inventors: Wolfgang Koller; Theodor Papenfuhs, both of Frankfurt am Main, Fed. Rep. of Germany

[73] Assignee: Hoechst Aktiengesellschaft, Frankfurt am Main, Fed. Rep. of Germany

[21] Appl. No.: 745,921

[22] Filed: Jun. 18, 1985

[30] Foreign Application Priority Data

Jun. 20, 1984 [DE] Fed. Rep. of Germany ....... 3422807

[51] Int. Cl.$^4$ ............................................. C07C 87/60
[52] U.S. Cl. ................................................... 564/441
[58] Field of Search ........................................ 564/441

[56] References Cited

U.S. PATENT DOCUMENTS

3,184,387  5/1965  Seemuller ............................ 564/441
3,274,249  9/1966  Brunner et al. ...................... 564/441
3,743,678  7/1973  Halasz ................................. 564/441

FOREIGN PATENT DOCUMENTS

0019158  9/1982  European Pat. Off. .

OTHER PUBLICATIONS

Sidgwick's Organic Chemistry of Nitrogen, 3rd Edition Oxford University Press, London 1966 pp. 95–96.
Beilsteins *Handbuch der Organischen Chemie* XIII, p. 389.
Beilsteins *Handbuch der Organischen Chemie* EII, p. 193.
*Comprehensive Organic Chemistry*, vol. 2, ed., Sutherland, I. O., Pergamon Press, Oxford, 1979, p. 161.

Primary Examiner—Charles F. Warren
Assistant Examiner—R. A. Picard
Attorney, Agent, or Firm—Connolly and Hutz

[57] ABSTRACT

A process for the preparation of pure 2-ethylamino-4-nitro-1-alkoxybenzenes of the formula (1)

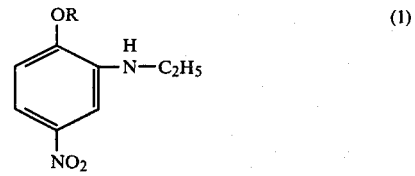

in which R denotes an alkyl($C_1$–$C_4$) or alkoxy($C_1$–$C_4$)-alkyl($C_1$–$C_4$) group, which comprises N-monoalkylation of 2-amino-4-nitro-1-alkoxybenzenes of the formula (2)

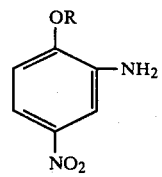

in which R has the abovementioned meaning, using a slight excess of diethyl sulfate in non-polar, organic solvents in the absence of water at temperatures of about 40° to about 120° C.

2 Claims, No Drawings

PROCESS FOR THE PREPARATION OF PURE 2-ETHYLAMINO-4-NITRO-1-ALKOXYBENZENES

The present application relates to a process for the preparation of pure 2-ethylamino-4-nitro-1-alkoxybenzenes by selective mono-N-alkylation of 1-alkoxy-2-amino-4-nitrobenzenes with diethyl sulfate.

It is known to prepare 1-alkoxy-2-amino-4-nitrobenzenes by partial reduction of 2,4-dinitroalkoxybenzenes (Beilstein XIII, page 389) or by nitration of o-acetaminophenol ethers and subsequent deacylation (Beilstein E II, 13, page 193). As our own investigations have shown, N-alkylation of 1-alkoxy-2-amino-4-nitrobenzenes prepared in this way does not, however, lead to homogeneous products but to product mixtures composed of non-alkylated primary amines, N-monoalkylated secondary amines and N,N-dialkylated tertiary amines in each case. This is in agreement with data in the literature according to which N-alkylation of primary aromatic amines usually leads to a mixture of the three types of compound mentioned. [R. J. Lindsay in "Comprehensive Organic Chemistry", Pergamon Press, Oxford, 1979, Volume 2, page 161].

This inevitably meant that the coupling component which is necessary for the preparation of valuable blue disperse azo dyestuffs and which takes the form of the acyl compound of the formula

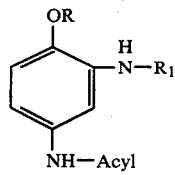

in which R has the meaning given below and $R_1$ represents a lower alkyl group (obtainable by reduction and subsequent acylation of 2-alkylamino-4-nitro-1-alkoxyphenols), likewise could not be used as a homogeneous compound but only in the form of a corresponding amine mixture, which resulted in poor yields of dyes and in dulled dye mixtures.

If homogeneous disperse azo dyes were required instead of mixtures of dyes, up to now it has been necessary to work with protecting groups in order to obtain the required monoalkylation. Thus for example, the amino group attached to the aromatic nucleus of 1-alkoxy-2-amino-4-nitrobenzene can be converted into the N-formyl group with formic acid (EP No. 0,019,158). The N-formyl compound thus obtained can subsequently be alkylated with dialkyl sulfate and the N-formyl group can then be eliminated again with alkali metal hydroxide solution.

Surprisingly, it has now been found that pure 2-ethylamino-4-nitro-1-alkoxybenzenes of the formula (1)

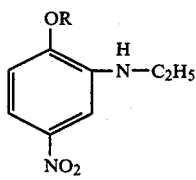

in which R denotes an alkyl($C_1$–$C_4$) or alkoxy($C_1$–$C_4$)alkyl($C_1$–$C_4$) group, can be prepared by selective N-monoalkylation of 2-amino-4-nitro-1-alkoxybenzenes of the formula (2)

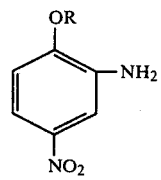

in which R has the abovementioned meaning (without prior introduction and subsequent elimination of protecting groups), using a slight excess of diethyl sulfate in non-polar, organic solvents in the absence of water.

Examples of suitable, non-polar, organic solvents are toluene, chlorotoluenes, chlorobenzenes, xylenes, heavy gasoline and naphtha (=technical mixture of ethylbenzene and xylenes) and mixtures of the abovementioned solvents.

In contrast, alkylation in polar solvents such as, for example, methanol or water leads to considerable quantities of non-alkylated amine and N-dialkylated amine.

The process according to the invention is carried out in detail as follows:

1.1 to 1.5 mole of diethyl sulfate is run into a mixture of 1 mole of 2-amino-4-nitro-1-alkoxybenzene of the abovementioned formula (2) in 300 to 600 ml, preferably 400 ml, of a non-polar, organic solvent such as, for example, heavy gasoline, naphtha or toluene and the mixture is stirred for 1 to 24 hours, preferably 5 hours, at about 40° C. to about 120° C., preferably at 80° C. The reaction mixture is then neutralized with 5–15% strength aqueous ammonia, the organic solvent used is removed by azeotropic distillation and the aqueous residue is adjusted to pH 0.4 with concentrated hydrochloric acid. To the mixture obtained are added a filtration aid, eg. kieselguhr, and small amounts of zinc dust, and the mixture is boiled under reflux for 20–60 minutes, preferably 30 minutes, and then filtered hot. Finally the solution is adjusted to pH 2 with concentrated sodium hydroxide solution and the precipitate is filtered off with suction and dried in vacuo.

2-Ethylamino-4-nitro-1-alkoxybenzenes of the said formula (1) are obtained pure and in high yield by the process according to the invention. The yields amount to 85–90% of theory, based on the 2-amino-4-nitro-1-alkoxybenzene used of the formula (2). The 2-ethylamino-4-nitro-1-alkoxybenzenes thus obtained can be converted in a known manner and in high yields by catalytic hydrogenation and subsequent acylation into the corresponding, industrially valuable, homogeneous 2-ethylamino-4-acylamino-1-alkoxybenzenes which serve as coupling components in the preparation of blue disperse azo dyes [Belgian Pat. No. 634,032]. As a result of obtaining compounds of the formula (1) in pure form it is possible, via the 2-ethyl-amino-4-acylamino-1-alkoxybenzenes, which can be prepared from them, also to prepare the blue disperse azo dyes in homogeneous form and in good yield and with improved coloristic properties. Moreover, the manufacturing difficulties otherwise arising when amine mixtures are obtained can be avoided by obtaining compounds of the formula (1) in pure form according to the invention.

EXAMPLE 1

(2-Ethylamino-4-nitro-β-methoxyethoxybenzene)

200 g of diethyl sulfate (1.3 mole) are added dropwise to a mixture of 579 g of heavy gasoline (fraction 120°–130° C.) and 212 g of 2-amino-4-nitro-β-methoxyethoxybenzene (1 mole). The mixture is stirred at 80° C. for 5 hours and then neutralized with 169 g of 14% strength aqueous ammonia. The heavy gasoline is removed by azeotropic distillation and the aqueous residue is adjusted to pH 0.4 with 165 g of concentrated hydrochloric acid. 10 g of kieselguhr and 0.5 g of zinc dust are added to the mixture. It is then boiled under reflux for 30 minutes and finally filtered hot. The filtrate is adjusted to pH 2 with 120 ml of concentrated sodium hydroxide solution. The precipitate is filtered off with suction and dried in vacuo.

230.4 g of 2-ethylamino-4-nitro-β-methoxyethoxybenzene are obtained, which corresponds to a yield of 88% of theory.

Melting point: 83°–87° C.

| Gas chromatographic analysis: | |
| --- | --- |
| 2-Amino-4-nitro-β-methoxyethoxybenzene | 5% |
| 2-Ethylamino-4-nitro-β-methoxyethoxybenzene | 92% |
| 2-Diethylamino-4-nitro-β-methoxyethoxybenzene | 2% |

EXAMPLE 2

(2-Ethylamino-4-nitro-β-methoxyethoxybenzene)

185 g of diethyl sulfate (1.2 mole) are added dropwise to a mixture of 577 g of toluene and 212 g of 2-amino-4-nitro-β-methoxyethoxybenzene (1 mole). The mixture is stirred at 80° C. for 5 hours and then neutralized with 169 g of 14% strength aqueous ammonia. The toluene is removed by azeotropic distillation and the aqueous residue is adjusted to pH 0.4 with 165 g of concentrated hydrochloric acid. 10 g of kieselguhr and 0.5 g of zinc dust are added to the mixture. It is then boiled under reflux for 30 minutes and finally filtered hot. The filtrate is adjusted to pH 2 with 120 ml of concentrated sodium hydroxide solution. The precipitate is filtered off with suction and dried in vacuo. 215 g of 2-ethylamino-4-nitro-β-methoxyethoxybenzene are obtained, which corresponds to a yield of 76% of theory.

Melting point: 82°–85° C.

| Gas chromatographic analysis: | |
| --- | --- |
| 2-Amino-4-nitro-β-methoxyethoxybenzene | 9% |
| 2-Ethylamino-4-nitro-β-methoxyethoxybenzene | 85% |
| 2-Diethylamino-4-nitro-β-methoxyethoxybenzene | 4% |

We claim:

1. A process for the preparation of pure 2-ethylamino-4-nitro-1-alkoxybenzenes of the formula (1)

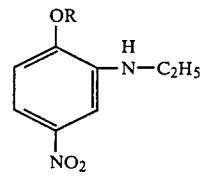

(1)

in which R denotes an alkyl($C_1$–$C_4$) or alkoxy($C_1$–$C_4$)alkyl($C_1$–$C_4$) group, which comprises N-monoalkylation of 2-amino-4-nitro-1-alkoxybenzenes of the formula (2)

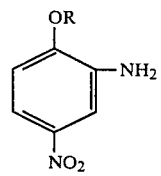

(2)

in which R has the abovementioned meaning, using a slight excess of diethyl sulfate in non-polar, organic solvents in the absence of water at temperatures of about 40° to about 120° C.

2. The process as claimed in claim 1, which comprises alkylation in toluene, chlorotoluenes, chlorobenzenes, xylenes, heavy gasoline, naphtha or mixtures of these.

* * * * *